United States Patent [19]
Tournier et al.

[11] Patent Number: 5,910,300
[45] Date of Patent: Jun. 8, 1999

[54] AMPHIPHILIC LINKERS FOR COUPLING ADMINISTRABLE DIAGNOSTICALLY OR PHYSIOLOGICALLY ACTIVE AGENTS AND BIOSELECTIVE TARGETING COMPOUNDS

[75] Inventors: Hervé Tournier, Valleiry, France; Sibylle Pochon; Bernard Lamy, both of Geneva, Switzerland

[73] Assignee: Bracco Research S.A., Switzerland

[21] Appl. No.: 08/740,620

[22] Filed: Oct. 31, 1996

[30] Foreign Application Priority Data

Nov. 1, 1995 [EP] European Pat. Off. ............... 95810689

[51] Int. Cl.$^6$ .......................... A61K 49/00; G01N 31/00
[52] U.S. Cl. ............................ 424/9.34; 424/9.1; 424/9.3
[58] Field of Search ..................... 424/1.11, 9.1, 424/9.3, 9.34, 9.5; 128/653.2, 654, 662.02, 660.01, 653.1; 428/403, 407; 436/173, 525, 526

[56] References Cited

U.S. PATENT DOCUMENTS

| | | | |
|---|---|---|---|
| 4,070,246 | 1/1978 | Kennedy et al. | 195/99 |
| 4,157,323 | 6/1979 | Yen et al. | 260/29.7 |
| 4,628,037 | 12/1986 | Chagnon et al. | 436/526 |
| 4,762,915 | 8/1988 | Kung et al. | 530/405 |
| 4,904,479 | 2/1990 | Illum | 424/490 |
| 4,986,979 | 1/1991 | Morgan, Jr. et al. | 424/1.11 |
| 5,069,216 | 12/1991 | Groman et al. | 128/653.4 |
| 5,271,927 | 12/1993 | Parker et al. | 424/9.1 |
| 5,284,646 | 2/1994 | Menz et al. | 424/9.1 |
| 5,314,679 | 5/1994 | Lewis et al. | 424/9.1 |
| 5,395,609 | 3/1995 | Stuttle | 424/1.69 |
| 5,464,696 | 11/1995 | Tournier et al. | 428/403 |
| 5,516,703 | 5/1996 | Caldwell et al. | 436/532 |
| 5,545,395 | 8/1996 | Tournier et al. | 424/9.32 |
| 5,552,525 | 9/1996 | Dean | 530/326 |
| 5,587,199 | 12/1996 | Tournier et al. | 427/2.12 |
| 5,593,622 | 1/1997 | Yoshroka et al. | 264/4.32 |
| 5,653,959 | 8/1997 | Tournier et al. | 424/9.32 |

FOREIGN PATENT DOCUMENTS

| | | |
|---|---|---|
| 0398143 | 11/1990 | European Pat. Off. . |
| 0 426 488 A1 | 5/1991 | European Pat. Off. . |
| 0 605 963 A2 | 7/1994 | European Pat. Off. . |
| 0605963 | 7/1994 | European Pat. Off. . |
| 43 09 333 A1 | 9/1994 | Germany . |
| 8601112 | 2/1986 | WIPO . |
| WO 86/01112 | 2/1986 | WIPO . |
| WO88/00060 | 1/1988 | WIPO . |
| WO 94/04197 | 3/1994 | WIPO . |
| 9421240 | 9/1994 | WIPO . |
| WO 95/06251 | 3/1995 | WIPO . |
| 9716474 | 5/1997 | WIPO . |

OTHER PUBLICATIONS

Topchiyeva Polymer Science USSR 32 (1990) No. 5 pp. 833–851 Synthesis of Biologically Active Polyethylene Glycol Derivatives. A Review.

*Primary Examiner*—Jose' G. Dees
*Assistant Examiner*—Dameron Jones
*Attorney, Agent, or Firm*—Nixon & Vanderhye

[57] ABSTRACT

Administrable factors or compositions to be directed to specific sites in the body of human and animal patients which comprise a medically and/or diagnostically effective moiety (I) and, coupled thereto by means of a linker (L), a substance (II) having specific affinity for specific sites in the organism.

Linker "L" has a structure schematized by the formula:

$$Y(W\text{-}Z\text{-}R)_m, \text{ m being 1, 2, or 4}$$

wherein the portion YW is an amphiphile, i.e. a segment comprised of a hydrophobic-lipophilic sequence "Y" and a hydrophilic-lipophobic sequence "W" connected covalently together, Z is a chemical bond or an intermediate connector sequence and R is a reactive function for effecting coupling with selected substances (II).

23 Claims, 3 Drawing Sheets

AMPHIPHILIC LINKERS FOR COUPLING ADMINISTRABLE DIAGNOSTICALLY OR PHYSIOLOGICALLY ACTIVE AGENTS AND BIOSELECTIVE TARGETING COMPOUNDS

FIELD OF THE INVENTION

The present invention concerns administrable molecular conjugate systems or compositions comprising magnetically tagged vectors to be directed to specific sites in the body of human and animal patients for magnetic resonance imaging purposes.

Systems of this kind are comprised of a magnetically responsive signal generator moiety (I) and, coupled thereto by means of a bond or a linker (L), a substance (II), for instance a protein, a peptide or a bioactive substrate having specific affinity for specific sites in the organism, i.e. specific organs or tissues which need to be visualized. Actually, moiety (II) acts as an arrowhead or homing factor to direct and transport signal generating moiety (I) to specific targets in the body via the circulation or otherwise. Optionally, (II) may also mediate endocytosis of (I).

The present invention particularly concerns novel intermediates (I-L and L-II) and systems represented by the ternary structure (I-L-II).

BACKGROUND OF THE INVENTION

The use of administrable conjugates systems in which biomolecules (II) targeted to specific sites or receptors in the organism of patients are coupled to diagnostically active ligands (I) acting as signal generator means to provide diagnostically useful information has become widely known in recent years.

The diagnostically active agents may include materials capable of generating a response signal to be picked-up by suitable receiving instruments, electronically processed and converted to display. For instance, an electromagnetic signal can be detected and processed by appropriate equipment, and finally converted to data medically interpretable by suitably trained personnel. Among diagnostically active agents, one may cite radionuclides (β- or γ-emitters) detectable by counting and scintillation, iodinated X-ray opacifiers which provide a contrast effect in radio-investigations, magnetically responsive materials (ferromagnetic, paramagnetic and super-paramagnetic substances) which provide contrast effects in magnetic resonance imaging (MRI), and microbubbles as well as microballoons which provide contrast effects in ultrasonic echographic imaging.

The coupling in the foregoing conjugates generally relies on the assistance of a bond or a linker (L) having chemically reactive functions designed to effect covalent bonding between moieties (I) and (II). A number of systems which can be presented by the general formula (I-L-II) i.e. systems comprising moieties (I) and (II) connected chemically by a linker (L) are known in the art.

Many different proposal known include for instance, polymeric microspheres containing magnetically active $Fe_3O_4$ particles in which mainly acrylics polymers containing reactive functions, for instance polyacrylamide, polyacrylic acid and the like, are tagged with covalently bonded fluorescent dyes, lectins, antigens, antibodies and other biologically active substances, thus allowing detection and localization of specific carbohydrates residues, hormone receptors and other specific cell surface components.

Superparamagnetic metal oxide particles usable in-vivo for the diagnostic localization of cells or tissues recognized by a particular bioaffinity adsorbent coupled to the particles and also for magnetically directing therapeutically active agents coupled to the particles to pathological sites have also been proposed. The magnetic particles attached to a silane linker by a silanization reaction involving reactive silanes $R—Si(OX)_3$ in which X is a lower alkyl and R represents any aliphatic or aromatic sequence terminating in $—NH_2$, $—OH$, $—SH$, aliphatic hydrophobic, or amphipatic function are reported to be suitable for covalently coupling to a bioaffinity absorbent.

Similarly, administrable magnetic microparticles (for instance magnetite) coupled to substances having binding affinity for organic tissues have also been known. Thus for example, tissue-specific substances such as antibodies, neurotransmitters, hormones, metabolites, enzymes, toxins, and natural or synthetic drugs have been coupled to magnetite particles by coating the particles biodegradable polymers carrying reactive functional groups and linking to the tissue-specific substances through said reactive groups. The tissue-specific targeted magnetite microparticles administered by injection into the blood stream are thus transported to targeted organs or tissues where they operate as contrast enhancers in MRI investigations of said organs.

Methods and reagents for the in-vivo tagging of polymorphonuclear leukocytes (PMN), e.g. lymphocytes, with a medically useful metal ion, including radioisotopes and paramagnetic elements, and subsequent detection of the PMN trafficking and sites of concentrated leukocytes within the organism by radiodetection or MRI have also been suggested. In the suggested method there is administered an effective amount of a formulation comprising a leukostimulatory reagent (a lectin) bound to a useful metal species under conditions allowing the reagent to attach to leukocytes, whereby the concentrations of the stimulated leukocytes are subsequently ascertained by detection and quantitation of the metal using conventional measuring means.

EP-A-0 398 143 (A. J. Fischman et al.) discloses labeled chemotactic peptides to image focal sites of infection or inflammation. The labeled peptides described in this reference are schematized by the formula

N(X)-Y-Leu-Phe-Z-W where N is nitrogen, X is a protective formyl, acetyl or t-Boc group; Y is methionine or norleucine; W is a label, e.g. an EDTA or DTPA chelate of a radioactive or paramagnetic isotope and Z is a covalent bond or a linker sequence. The reference also describes the injection of the radioactive labeled chemotactic peptides into experimental rats previously infected in the thighs with strains of *E. coli*, and the subsequent localization of the infection sites by hourly serial γ-camera images.

Moreover, derivatized hydrophilic-hydrophobic bloc copolymers have been disclosed to bridge substrates to targeting proteins. For instance, WO-A95/06251 (University of Utah) discloses derivatized Pluronic® and Tetronic® compounds carrying reactive groups at the end of the PEG blocks. The derivatized copolymers are used to coat by adsorption hydrophobic surfaces (e.g. polystyrene beads and similar carriers), which coated surface then function as substrates for immobilizing proteins and alike substances (applications: e.g. ELISA tests).

Although the achievements of the prior art have merit, they may suffer from some inevitable drawbacks related to preparing the systems of the general formula (I-L-II) by conventional chemical means which are tedious and costly.

Another disadvantage of the systems known so far is linked to the problem of metabolisations or elimination from the body of these complex molecules which once served their purpose i.e. imaging of the targeted tissue do not have further purpose or reason d'etre. When such complex systems are used to deliver a therapeutic agent to a given site, the depletion of the therapeutically active substance simultaneously causes at least a partial digestion and susequent elimination of the complex molecule. However, when such systems are used for imaging elimination of the used molecule becomes a problem.

The present invention in which there are also used the linker properties of derivatized hydrophobic-hydrophilic bloc copolymers constitute a serious advance toward simplification of the coupling between the magnetically responsive moieties (I) and the homing proteins or peptides (II).

SUMMARY OF THE INVENTION

A first object of the invention is to provide novel administrable conjugate systems of the formula (I⇌-L-II) wherein (I) represents a magnetically responsive moiety capable of providing contrast in MRI, i.e. acting as a factor of contrast in the image display; L is a linker or bridging unit derived from a suitably funtionalized hydrophobic-hydrophilic bloc copolymers such as Pluronic®, Tetronic®, Synperonic® or the like; and (II) is tageting unit such as peptide, protein or other bioactive substance having affinity for specific sites, organs or tissues in the body.

The novel systems are characterized in that although the bond between L and (II) is covalent, the bond between (I) and L is non-covalent, preferably a bond by affinity controlled by Van de Waals forces, which results in considerable molecular mobility in aqueous carrier media and excellent resistance of the conjugate to opsonization after injection in the circulation. In view of this characterizing parameter, it is preferred to symbolize the novel adducts by the formula IfL-II.

Evidently, the injection of such systems IfL-II into the circulation for transporting ligand I to specific targeted sites is also an object of the invention.

The linkers L may have the formula (i)

$Y(W-Z-R)_m$, m being 1, 2, or 4    (i)

wherein the portion YW is a segment comprised of a hydrophobic-lipophobic sequence "Y" for non-covalently binding with moiety (I) and a hydrophilic-lipophobic sequence "W" connected covalently together, Z is a chemical bond or an intermediate connector sequence [for instance a $C_1$–$C_4$ aliphatic segment] and R is a reactive function for effecting covalent coupling with selected bioactive targeting compounds (II).

In a variant, the linkers can be represented by "L'" and schematized by the formula (ii):

$L'=(RZWY)_2N-Y^1-N(YWZR)_2$    (ii)

where N is nitrogen, and in which Y, W, Z, and R are defined as in formula (i), although 1 to 3 R's can be H, and $Y^1$ is a hydrophobic bridging sequence, e.g. a sequence like Y, namely an aliphatic chain optionally interrupted by heteroatoms, for instance a $C_2$–$C_6$ alkylene, or $=N(CH_2)_{2-6}N=$. The linkers L' have properties similar to that of linkers L but with available polyfunctionality, i.e. they may effect coupling with up to four targeting units.

Another object of the invention is a method for making the linkers (L or L') according to the foregoing structures, which comprises functionalizing an amphiphilic surfactant compound YWm [or $(WY)_2NY^1N(YW)_2$], m being 1 or 2, in which "Y" is a lipophilic and hydrophobic sequence and "W" is a hydrocompatible sequence having oil-in-water dispersing properties and terminated with —OH or —$NH_2$, by reacting it with reactants suitable to provide reactive functions R selected from —$NHNH_2$, —CHO (free or in the form of dialkyl acetal), —CH=N—$NH_2$, —NCO, NCS, —CO—NH—$NH_2$, —O—CO—NH—$NH_2$, —COOH, —SH, —COCl, —O—COCl, and the like.

Still another object is a method in which the linkers L (or L') are covalently bound, via reactions involving function R, to targeting vectors (II) to make intermediates (L-II) suitably designed to effect transportation to specific sites in the organism.

In this invention, the lipophilic sequence Y is selected to attractively bind (non-covalently) to alike sequences of the signal generator moiety (I). As said above, in this description, this type of binding is denoted by a f. Hence, depending on the nature of Y, the binding force to link with the signal generator (I) can be modulated, which enables to adequately control the stability of systems (IfL-II) as well as their life-time before metabolization after administration to the body. This structure also enables easier degradation (with optional release of active species) and post-elimination from the organism.

Hence, a further object is to provide non-covalent intermediates (IfL) in which (I) and L are defined as above, and methods of making such intemediates (IfL) by non-covalently binding the linkers L (or L') to a magnetically active signal generator ligand (I), the connection being by mutual attractive forces between the lipophilic sequence Y of L and alike sequences of said ligand (I).

DETAILED DESCRIPTION OF THE INVENTION

Figure 1:
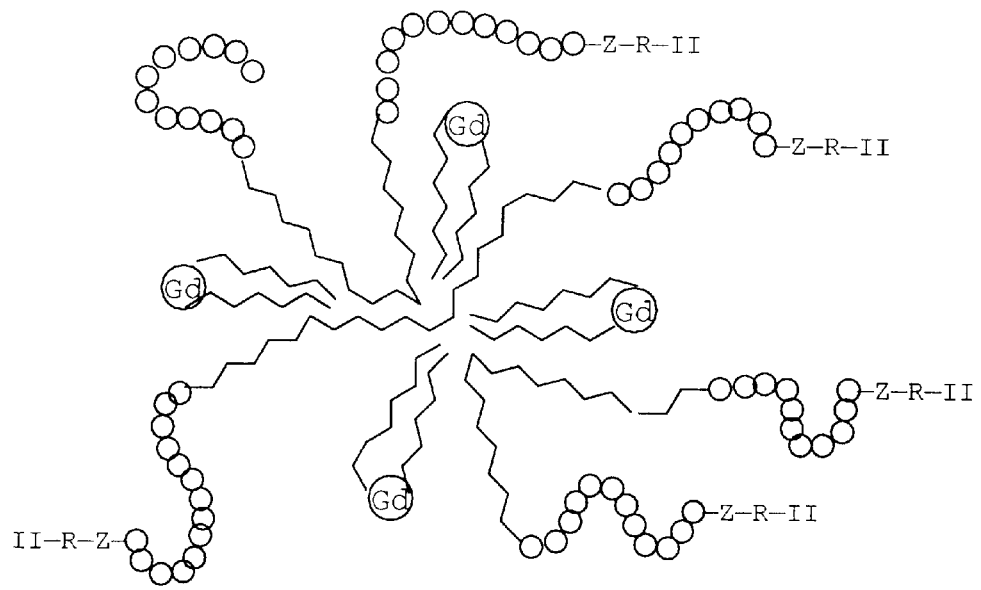
FIG. 1 is a schematic representation of an embodiment of a system IfL-II according to the invention. In this embodiment gadolinium chelates (large circles marked Gd) are provided with hydrophobic segments (plain lines) whose hydrophobic segments associate by affinity with corresponding segments (Y) of an amphiphilic linker (L) whose hydrophilic segments (W) (small circles) are derivatised (-ZR-) and coupled with arrowhead II.

The main aspect of the invention as set out in the accompanying claims are based on the unexpected finding that administrable conjugate systems of the formula (I-L-I) wherein (I) represents a magnetically responsive moiety capable of providing contrast in MRI, i.e. acting as a factor of contrast in the image display; L is a linker or bridging unit derived from a suitably functionalized hydrophobic-hydrophilic bloc copolymers such as Pluronic®, Tetronic®, Synperonic® or the like; (II) is tageting unit such as peptide, protein or other bioactive substance having affinity for specific sites, organs or tissues in the body, and the bond between L and (II) is covalent, the bond between (I) and L is non-covalent posses all the advantages of the systems in which both bonds are covalent but their metabolisation i.e. elimination is much faster.

The novel systems are characterized by the fact that although the bond between L and (II) is covalent, the bond between (I) and L is non-covalent, preferably a bond by affinity controlled by Van de Waals forces, which results in considerable molecular mobility in aqueous carrier media and excellent resistance of the conjugate to opsonization after injection in the circulation. In view of this characterizing parameter, it is preferred to symbolize the novel adducts by the formula IfL-II.

Evidently, the injection of such systems IfL-II into the circulation for transporting ligand I to specific targeted sites is also an object of the invention.

The linkers L may have the formula (i)

Y(W-Z-R)$_m$, m being 1, 2, or 4    (i)

wherein the portion YW is a segment comprised of a hydrophobiclipophilic sequence "Y" for non-covalently binding with moiety (I) and a hydrophilic-lipophobic sequence "W" connected covalently together, Z is a chemical bond or an intermediate connector sequence [for instance a $C_1$–$C_4$ aliphatic segment] and R is a reactive function for effecting covalent coupling with selected bioactive targeting compounds (II).

In a variant, the linkers can be represented by "L'" and schematized by the formula (ii):

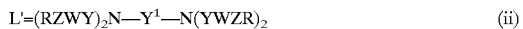

L'=(RZWY)$_2$N—Y$^1$—N(YWZR)$_2$    (ii)

where N is nitrogen, and in which Y, W, Z, and R are defined as in formula (i), although 1 to 3 R's can be H, and Y$^1$ is a hydrophobic bridging sequence, e.g. a sequence like Y, namely an aliphatic chain optionally interrupted by heteroatoms, for instance a $C_2$-$C_6$ alkylene, or =N(CH$_2$)$_{2-6}$N=. The linkers L' have properties similar to that of linkers L but with available polyfunctionality, i.e. they may effect coupling with up to four targeting units.

In the linkers, when m=1 or 2, the sequence Y may usually be a hydrophobic lipophilic aliphatic or aryl-aliphatic sequence optionally interrupted by hetereoatoms such as O, N and S. When m is 4, Y has advantageously the formula A(Y')$_4$ in which A and Y' also correspond to the foregoing definitions for Y; for instance, in this case A may preferably be a group of formula —(CH$_2$)$_p$ or =N(CH$_2$)$_p$N=, in which p is an integer from 2 to 6.

Thus, Y is preferably chosen within classes of compounds comprising sequences selected from sterols (e.g. cholesterol, lanosterol, ergosterol, coprostanol, tocopherol and the like), the alkyl moiety of long chain alcohols (e.g. $C_{10}$–$C_{18}$ alcohols), long chain acids (e.g. fatty acids), long chain polyglycerides (e.g.the alkyl part of mono-, di-, and triglycerides), alkyl-phenols, -amines and -amides, hydrophobic polyoxyalkylenes, and the like. Other examples may include hydrophobic polyanhydrides, polyorthoesters, polyphosphazenes, polyhydroxy acids, polycaprolactones polylactic, polyglycolic polyhydroxy-butyric acids. "Y" may advantageously contain repeating short aliphatic chains, such as propylene, isopropylene, butylene, isobutylene, pentamethylene and the like separated by oxygen atoms. In practice, a preferred Y comprises from about 10 to 60 hydrophobic alkyleneoxy units, preferably propyleneoxy. In general, the criteria for best selection of the nature of Y is its affinity for alike groups attached to moiety (I) as will be disclosed more fully hereafter.

In order to be operative in the sense of the present invention, the hydrophilic properties of the sequence W of the linker should preferably be such as to promote easy dispersion of systems of structure (IfL-II) in aqueous liquids. Hence, there should be an appropriate matching of the lipophilicity of Y and the hydrophilicity of W for proper operation. In practice, the HLB balance should preferably be around 10–35, preferably 25–30, although this range may be overcome if necessary in special cases. "W" can be ionic, e.g. sulfonate, polyphosphate and the like, but preferably, W should be non-ionic, i.e. including structures such as hydrophilic polyoxyalkylenes, sugars and sugar derivatives, hydrophilic cellulose derivatives (e.g. hydroxymethyl cellulose and analogs), tertiary amine oxides, crown ethers, sorbitan rings and similar hydrophilic cyclic compounds. Advantageous structures for W are that of polyethyleneoxy, and polymethyleneoxy sequences. In the case of W being a polyethyleneoxy chain, the number of polyethyleneoxy units may be 5–300, but preferably about 50 to 150.

In common practice, one may interestingly perform the present invention using derivatized commercial surfactants of the kinds identified by the following labels: Pluronic®s, Synperonic®s, Poloxamer®s, L38, F38, L42, L44, L61, L62, L62LF, L64, F68, P75, L81, P85, F108, L121, F127; Synperonic® T-series; Synperonic® L-series; BRIJ®; MYRJ®; Tween®, and the like.

The reactive functions R are very numerous and well known in the art. An exhaustive description of such functions and their preparation can be found in the documents cited herebefore in this specification, namely in the background art section, and which are incorporated herein by reference. The reactive functions include for instance the following groups: —OH, —NH$_2$ (or NR$^1$R$^2$ where R$^1$ and R$^2$ are H or lower alkyls), —CHO (free or in the form of dialkyl acetal), —CO—NH—NH$_2$, —O—CO—NH—NH$_2$, —COOH, —SH, —COCl, —O—COCl, etc. In the present invention, one preferably introduces such functions by end modification of the segment W as more fully detailed hereafter in the Examples.

The reactive functions enable to prepare intermediates of structure (L-II) by reacting a functionalized -W-R of the linker with a targeting substance. Among the targeting substances, one may cite the following ones including the respective targets.

| Homing factor | Target |
|---|---|
| Antibodies (and fragments such as Fab, F(ab)'2, Fv, Fc, etc. | RES system |
| Epidermal growth factor (EGF) | Cellular receptors |
| Collagen | Cellular receptors |
| Gelatin | Cellular receptors |
| Fibrin-binding-protein | Fibrin |
| Plasminogen activator | Thrombus |
| Urokinase inhibitors | Invasive cells |
| Somatostatin analogs | Cellular receptors |
| Lectin WGA) | Axones |
| f-Met-Leu-Phe | Neutrophils |

-continued

| Homing factor | Target |
|---|---|
| Selectin active fragments | Glycosyl structures |
| ELAM, GMP 140 | Leucocyte receptors |
| "RGD" proteins | Integrins, Granulocytes |
| IL-2 | Activated T-cell |
| CD4 | HIV infected cells |
| Cationized albumin | Fibroblasts |
| Carnitine | |
| Acetyl-, maleyl-proteins | Macrophage scavenger receptor |
| Hyaluronic acid | Cellular receptors |
| Lactosylceramide | Hepatocytes |
| Asialofoetuin | Hepatocytes |
| Arabinogalactan | Hepatocytes |
| Galactosylated particles | Kupffer cells |
| Terminal fucose | Kupffer cells |
| Mannose | Kupffer cells, macrophages |
| Lactose | Hepatocytes |
| Dimuramyl-tripeptide | Kupffer cells, macrophages |
| Fucoidin-dextran sulfate | Kupffer cells, macrophages |
| Sulfatides | Brain |
| Glycosyl-steroids | |
| Glycosphyngolipids | Other glycosylated structures |
| Hypoxia mediators | Infarted tissues |
| Amphetamines | Nervous system |
| Barbiturates | Nervous system |
| Sulfonamides | |
| Monoamine oxidase inhibitor substrates | Brain |
| Chemotactic peptides (*) | Inflammation sites |
| Muscarine and dopamine receptor substrates | Nervous system |

(*) Chemotactic peptides are useful for the detection and investigation of diseased or disordered tissue sites or organs in the body of human and animal patients, i.e. sites of infection, inflammation, or other trauma.

Putting intermediate (L-II) into contact with a convenient magnetically responsive signal generator ligand (I) in an aqueous carrier liquid involves effecting direct attachment and formation of targeted factor (IfL-II) and its dispersion within said carrier liquid. This is thought to be due to the nature of the lipophilic sequence Y in the linkers of the invention which is believed to intermingles or intertwines (possibly by adsorption or Van der Waals forces) with suitable lipophilic groups of ligand (I), for instance the alkyl residue of fatty alcohols or fatty acids.

In a preferred make and use embodiment of the linkers of the invention, one will couple a reactively derivatized polyalkyleneoxy block-copolymer $Y(WR)_2$ (Y being a polypropyleneoxy sequence, W being a polyethyleneoxy sequence and R being —$NH_2$) with a protein homing factor (for instance biotin-N-hydroxysuccinimide methyl ester) to provide an intermediate (L-II) of structure $Y(W\text{-biotin})_2$. When the latter, in an aqueous carrier liquid, is put in the presence of a fatty alcohol mono- or diester of DTPA (in form of chelate with a paramagnetic metal), coupling occurs and there is obtained a dispersion of a system (IfL-II) of structure $DTPAfY(W\text{-biotin})_2$, which upon injection, is directed to cellular receptors subjected to biotin-avidin activation. This is illustrated by the scheme of FIG. 1. Techniques of concern here that involve affinity coupling of unmodified polyoxyalkylene block-copolymers (e.g. Poloxamer®s, Pluronic®, Synperonic®) and "hydrophobized" DTPA paramagnetic chelates are disclosed in European patent application No.95810403.6 incorporated herein by reference. Indeed, exceptionally effective paramagnetic NMR contrast compositions have been obtained when, in addition to a paramagnetic metal ion complexed with a polyaminopolycarboxylate chelating agent having a lipophilic moiety, the imaging composition comprises a physiologically acceptable non-ionic surfactant or a mixture of non-ionic surfactants and preferably one or more amphipatic compounds such as phospholipids.

In this invention, the lipophilic sequence Y is selected to attractively bind (non-covalently) to alike sequences of the signal generator moiety (I). As said above, this type of binding is denoted by a f. Hence, depending on the nature of Y, the binding force to link with the signal generator (I) can be modulated, which enables to adequately control the stability of systems (IfL-II) as well as their life-time before metabolization after administration to the body. This structure also enables easier degradation (with optional release of active species) and post-elimination from the organism.

Figure 2:
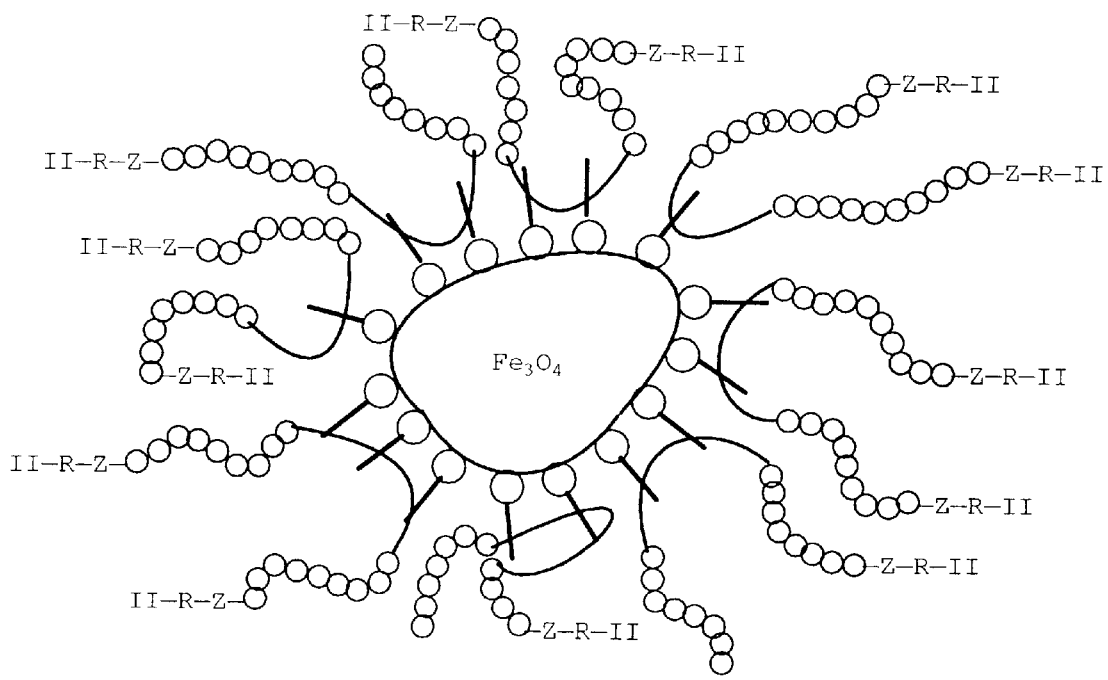
FIG. 2 is a schematic representation of another system according to the invention. In this embodiment, magnetite microparticles ($Fe_3O_4$), acting as MRI signal generator, are coated with a phosphatidic acid (circles with heavy side arm) whose hydrophobic moiety (straight arm) associates with the hydrophobic segments (plain rounded lines) of an amphiphile (YW). The hydrophilic portions (W) of the latter (small circles) are derivatized and coupled to a homing factor as in the previous embodiment of FIG. 1.
Figure 3:
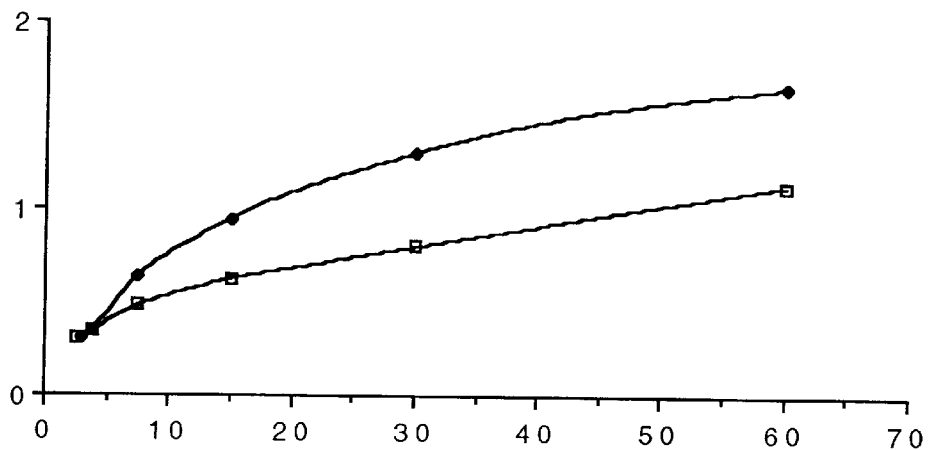
FIG. 3 is a graph showing the recognition by avidin of a molecular system comprising magnetic particles targeted with biotin via a linker according to the invention versus an untargeted system.

In another advantageous make and use embodiment of the present invention (see FIG. 2), one prepares an intermediate L-II, where L is derivatized Pluronic® F-108 and II is lactose, by linking together lactose isocyanate and the derivatised amphiphile bearing —$NH_2$ terminal groups at the polyethyleneoxy ends. One may then take advantage of the ready coupling of the lipophilic segment Y of said intermediate with the fatty acid residues of phospholipids to target toward hepatocytes for instance magnetite particles coated with phosphatidic acids, e.g. dipalmitoylphosphatidic acid (DPPA). The coating of magnetite particles with phospholipids is disclosed in publication WO-A-94/04197 (stealth magnetite particles) incoporated herein by reference.

The remarkable affinity of the Y segments of the linkers of the present invention and the fatty residues of phospholipids can be used to purposely tame liposome vesicles. For this, one may for instance refer to the incorporation of amphiphilic substances (see EP-A-0 354 855) to the phospholipids making the envelope of liposomic drug-carrier vesicles, said amphiphilic substances being of a nature similar to that which constitute the portion YW of the present linkers. In the techniques disclosed in the foregoing document, the hydrophobic portion of the amphiphile is sunk in the membrane-constituting lipids, while the hydrophilic portion protrudes therefrom and extends into the surrounding aqueous medium.

If, by analogy with the foregoing, one uses as the amphiphile an intermediate (L-II) according to the present specification, i.e. a tagged structure comprising a conjugate of a hydrophilic-lipophilic compound WY and a labeling biospecific substance one obtains a system comprising targeted liposome vesicles. When the liposome contain, for instance, therapeutically or diagnostically active agents encapsulated therein, the latter can be administered and directed to specific sites in the organism. This technique is simple and supersedes ancient techniques (such as that disclosed for instance WO-A-86/04232) for targeting liposomes based on using, in the liposome forming lipids, components carrying grafted functional groups to subsequently bind to selected homing proteins. These known techniques may however adversely affect the vesicle entrapment properties of the lipids and their encapsulation stability; obviously, in the present invention this pitfall does not exist.

Another object of the invention is a method for making the linkers (L or L') according to the foregoing structures, which comprises functionalizing an amphiphilic surfactant compound YWm [or $(WY)_2NY^1N(YW)_2$], m being 1 or 2, in which "Y" is a lipophilic and hydrophobic sequence and "W" is a hydrocompatible sequence having oil-in-water dispersing properties and terminated with —OH or —$NH_2$, by reacting it with reactants suitable to provide reactive functions R selected from —$NHNH_2$, —CHO (free or in the form of dialkyl acetal), —CH=N—$NH_2$, —NCO, NCS, —CO—NH—$NH_2$, —O—CO—NH—$NH_2$, —COOH, —SH, —COCl, —O—COCl, and the like.

Still another object is a method in which the linkers L (or L') are covalently bound, via reactions involving function R, to targeting vectors (II) to make intermediates (L-II) suitably designed to effect transportation to specific sites in the organism.

The following Examples illustrate the invention.

EXAMPLE 1

Ten g of Pluronic® F-108 of formula H—$(O(CH_2)_2)_a$—$(OCH(CH_3)CH_2)_b$—$(O(CH_2)_2)_a$—OH, in which a=147 and b=48, (1.43 mEq OH) were dissolved under agitation in 40 ml of dry ethyl acetate (AcOEt), 255 mg (1.47 mEq) of carbonyldiimidazole (CDI) were added and stirring was continued for about ½ hr at room temperature. The solution was degassed and 396 mg (3 mEq) of t.Butyl carbazate (t.Bu—O—CO—NH—$NH_2$) were added. After a 24 hr rest, 40 ml of ether were added and the solution was allowed to crystallize overnight at 4° C . The solid was collected by filtration and recrystallized from AcOEt (or $CH_2Cl_2$) and ether; yield 9.37 g of F-108-di[hydrazidourethane-BOC].

The reactions are schematized as follows:

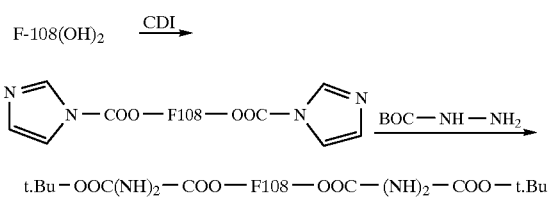

t.Bu—$OOC(NH)_2$—COO—F108—OOC—$(NH)_2$—COO—t.Bu

EXAMPLE 2

Twenty (20) g of Pluronic® F-108 of formula H—$(O(CH_2)_2)_a$—$(OCH(CH_3)CH_2)_b$—$(O(CH_2)_2)_a$—OH, in which a=147 and b=48, (2.86 mEq OH) were dissolved under agitation in 80 ml of dry ethyl acetate (AcOEt), 0.72 ml (3 mmol) of tri-n.butylamine N(n-Bu)$_3$ and 0.7 g (7 mmol) of succinic anhydride were added. The mixture was heated for 18 hr at 70° C., cooled to room temperature and filtered. After heating to 40° C., 40 ml of ether and 5 mmol of acetic acid (AcOH) were added and the mixture was allowed to crystallize overnight at 4° C. The solid was collected, suspended in 200 ml of ether, drained and dried. There were collected 19.74 g of F-108 diacid succinate of purity about 90% (ascertained by titration of the free carboxyl groups with 0.02N NaOH solution). The reaction was:

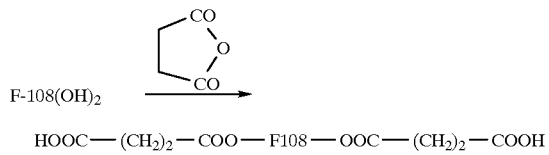

HOOC—$(CH_2)_2$—COO—F108—OOC—$(CH_2)_2$—COOH

EXAMPLE 3

In 20 ml of $CCl_4$ were dissolved 5 g (0.62 mEq COOH) of the F-108 diacid succinate as prepared in Example 2 and 0.3 ml (4.2 mmol, 6.5 eq in regard to COOH) of thionyl chloride were added. The mixture was refluxed for 2 hrs and the solvent removed completely on the rotavapor. To the residue were added 10 ml of dry AcOEt, then a solution of 1.32 g (10 mmol) of t.Bu-carbazate and 2.39 ml (10 mmol) of N(n.Bu)$_3$ in 8 ml of AcOEt. The yellow solution was heated for 1 hr at 50° C., then it was diluted with 40 ml ether and allowed to crystallize overnight at room temperature.

The solid (4.97 g) was dissolved in 10 ml of dry methylene chloride and 5 ml of tetrafluoracetic acid (TFA) were added. After 1.5 hr at room temperature, the solvents were removed on the rotavapor, 20 ml of AcOEt were added and the solution heated to 40° C., at which time 40 ml ether were added and the solution allowed to come back to r.t, whereby crystals formed. These were collected, dissolved in 20 ml AcOEt, 0.5 ml of N(n-Bu)3 were added, the solution was again heated to 40° C., diluted with 40 ml ether and allowed to cool to room temperature Then a further 30 ml ether were added and, after resting overnight, there were gathered 4.33 g of F108-dihydrazido succinate as ascertained by conventional hydrazide analysis (see below). The reactions were:

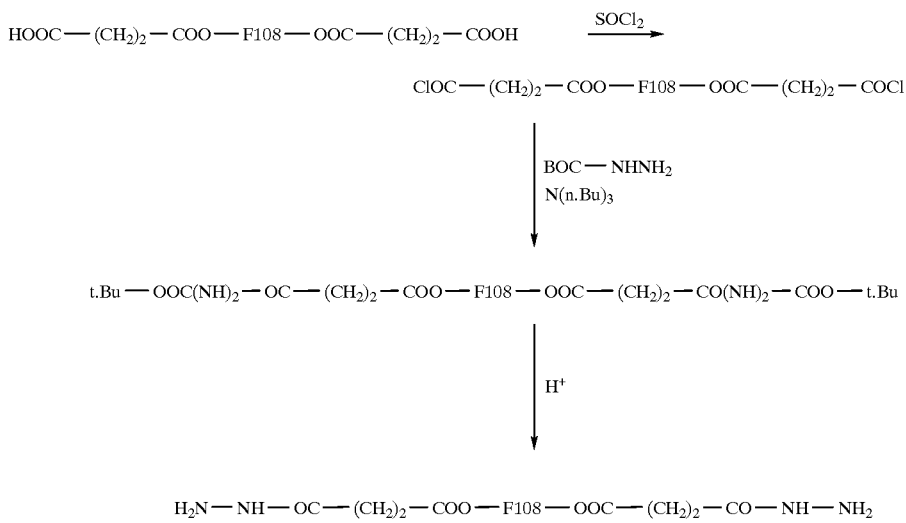

EXAMPLE 4

To a solution of 10 g (1.3 mEq) of F108 in 10 ml of $CCl_4$ were added 0.8 ml (3.6 mEq) of N(n.Bu)3, then at 0° C., 14.3 mEq of succinyl dichloride (as from Fluka A.G.). After allowing the black mixture to come back to room temperature, it was heated to 50° C. for 2.5 hrs, then it was allowed to cool and left aside overnight. The mixture was concentrated on the rotavapor to about 50 ml, and 200 ml of ether were added which caused fogging. The milky liquid was then poured into 600 ml of ether, whereby a greenish solid precipitated. This solid was redissolved, treated with charcoal and reprecipitated with ether from the filtered solution, which provided 8.84 g of the dichloride. If in the foregoing preparation there were used redistilled succinyl dichloride (46–47° C./0.7–0.9 Torr), the product obtained crystallized slowly after the addition of ether and charcoal purification was unnecessary. Also the yield was higher. The reaction is as follows:

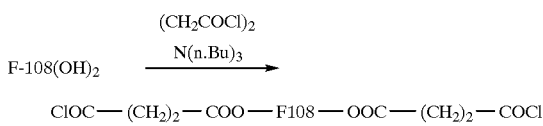

The dichloride was converted to the corresponding dihydrazide as disclosed in Example 3.

The dihydrazide compounds (from Examples 1–4) were analyzed spectrometrically (505 m, Kontron spectrometer) in aqueous solutions in the presence of trinitrobenzene sulfonate (TNBS) and potassium bisulfate. The measurements were done on solutions in the $10^{-5}$–$10^{-3}$ M range with reference to a calibration curve prepared from known diluted solutions of t.Bu-carbazate. The samples (1 ml) to be measured contained 0.8 ml of the hydrazide solution (control or test), 0.1 ml of 1M $KHSO_4$ and 1 ml of TNBS (1 g/L). The absorbance measurements were done 1 hr after preparing the samples, this delay being necessary to assure reproducibility. For the blank controls, distilled water was used.

The results showed that the techniques of Examples 1 and 4 were preferred to provide hydrazides with optimal purity and yields.

EXAMPLE 5

Five g (0.62 mEq —COOH) of the F108-diacid succinate (as obtained in Example 2) were dissolved (heating slightly was useful) in 20 ml of AcOEt and there were added ar room temperature 1 g (6 mmol) of CDI. The solution was left 30 min at room temperature, then it was heated to 50° C. for 3 hr. After allowing to stand 2 hr at room temperature, it was reheated to 50° C. and 50 ml ether were added, whereby a solid crystallized (4.91 g). This was collected, washed with ether and dried.

The solid was dissolved in 20 ml $CH_2Cl_2$ and to 10 ml thereof were added 400 mg (3 mmol) of t.Bu-carbazate in 1 ml of $CH_2Cl_2$. After 2 hrs at room temperature, 0.72 ml (3 mmol) of $N(n.Bu)_3$ were added and the mixture was left aside overnight. The product that crystallized out was collected and recrystallized in AcOEt/ether; yield 2.31 g. This product was deprotected by reacting with 4 ml of TFA in 4 ml of $CH_2Cl_2$ as in Example 3, and the solid obtained after removal of the solvents was crystallized from AcOEt/ether; yield 2.12 g. of F108-disuccinyl-hydrazide. Hydrazide analysis performed as disclosed above gave 2.96 mEq/g which is near theory.

The other 10 ml of solution of the di-imidazolyl-carbonyl derivative prepared above was treated with a solution containing 253 ml (3 mmol) of 1,3-diaminopropane and 0.72 ml (3 mmol) of tributylamine in $CH_2Cl_2$. After one night at room temperature, the solution was filtered and diluted with 50 ml ether which gave a solid. The latter was collected and recrystallized from successively AcOEt/ether and $CCl_4$/ether; yield 2.26 g of the di[aminopropylamidosuccinyl]-derivative of F108. The reactions are:

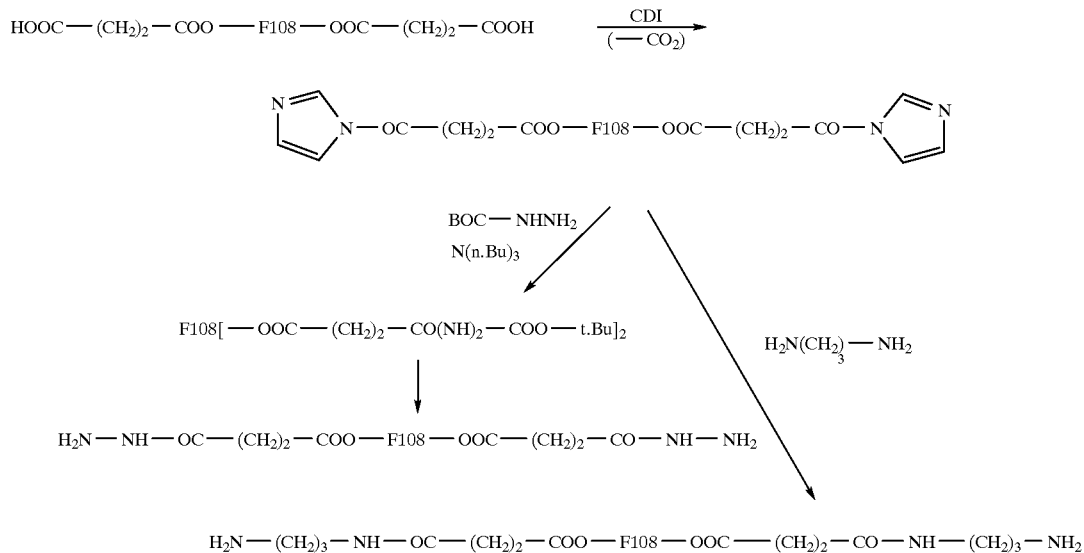

EXAMPLE 6

Five g of F108 (0.7 mEq) were dissolved in 10 ml of methylene chloride and 0.51 ml (2.15 mEq) of $N(n.Bu)_3$ were added. The solution was cooled to 0° C. and there were added 0.23 ml (2 mEq) of tresyl chloride. After allowing to slowly come back to room temperature (5 hrs). 10 ml of AcOEt were added, the solution was heated to about 50° C., 50 ml of ether were added and the whole was left to crystallize. After 2 days, the solid was separated by centrifugation (8000 g), washed with ether, dried, and dissolved in 20 ml of methylene chloride.

A 10 ml portion of this solution was treated with 400 mg (3 mmol) of t.Bu-carbazate in 1 ml of $CH_2Cl_2$. After 2 hrs at room temperature, 0.72 ml (3 mmol) of tributylamidne were added and the mixture was left overnight at room temperature Then 50 ml of ether were added, whereby a precipitate of F108-di(hydrazino-BOC) formed after several hrs at 4° C.; yield 2.11 g.

The above solid was dissolved in 4 ml of $CH_2Cl_2$ and de-protected with 4 ml TFA as disclosed in the previous Examples. After 1 hr at room temperature, the solvent was removed on the rotavapor and the residue was treated in 8 ml of AcOEt with 0.24 ml of tributylamine; addition of ether caused the precipitation of 2 g of the desired dihydrazino-F108.

The reactions are:

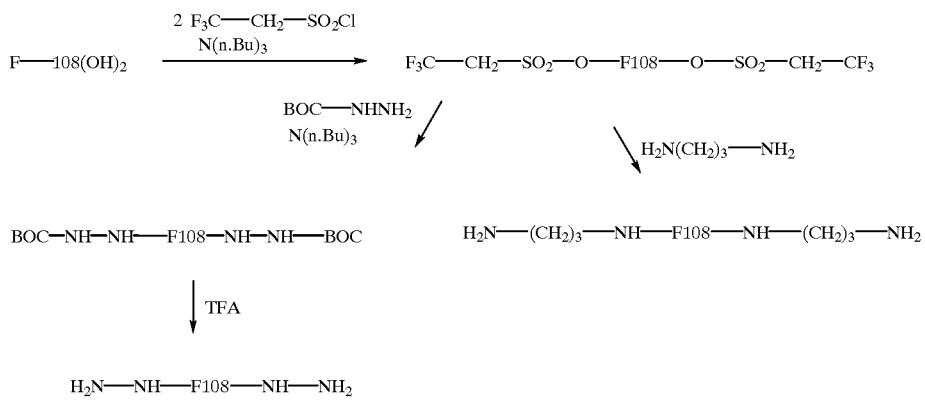

From the reaction scheme it follows that the corresponding di(aminopropylamino) compound was obtained from the other 10 ml of the ditresylate solution in methylene chloride by treatment with 3 mmol of 1,3-diaminopropane and 3 mmol of tri-n.butylamine at room temperature, precipitation with ether and crystallization from $CCl_4$/ether.

EXAMPLE 7

In a filtered solution of 21 g (3 mEq) of F108 in 80 ml of $CCl_4$, there were added at room temperature 1 ml (4.2 mEq) of tributylamine. After cooling, 2.2 ml (30 mmol) of thionyl chloride were added and the mixture was refluxed 4 hrs, whereby it turned red. It was filtered, stripped from the solvents, the residue redissolved in 80 ml of $CCl_4$ around 60° C. and 200 ml of ether were added which caused the precipitation of 20.3 g of solid; the latter was dissolved in AcOEt (80 ml) bleached with active charcoal, filtered and allowed to crystallize after the addition of 200 ml of ether. There were collected 19.06 g of the desired F108 dichloride. The reaction is schematized below.

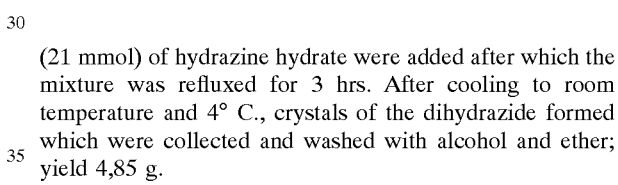

EXAMPLE 8

F108 (21 g, 3 mEq) were dissolved in 200 ml of toluene and the solvent was distilled off slowly to remove the moisture. After removal of about 120 ml of solvent, the solution was cooled and there were added 0.5 g (4 mmol) of potassium tert.butoxide. After 2 hrs of reflux the orange solution was cooled and 0.7 ml (6 mmol) of ethylbromoacetate were added. After resting overnight, the solution was refluxed for 2 hrs, cooled and filtered over celite. Addition of 200 ml of ether causes the formation 20.71 g of solid which were collected and crystallized from successively EtOH (100 ml)/ether (4° C.), and AcOEt (80 ml)/ether (200 ml). Yield 19.25 g.

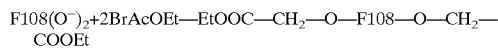

EXAMPLE 9

Five g of the diester from Example 8 (0.7 mEq) were dissolved in 25 ml of EtOH at about 50° C., and about 1 ml (21 mmol) of hydrazine hydrate were added after which the mixture was refluxed for 3 hrs. After cooling to room temperature and 4° C., crystals of the dihydrazide formed which were collected and washed with alcohol and ether; yield 4,85 g.

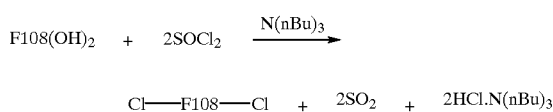

EXAMPLE 10

Ten g of the ethyl F108-diacetate from Example 8 were dissolved in a solution of 50 ml ETOH and 70 ml $H_2O$ and 3 ml of 32% NaOH were added. After 2 hrs at 50° C. and one night at room temperature, 15 g of salt were added, the pH was brought to 2 with conc. HCl and the mixture was extracted twice with 100 ml $CH_2Cl_2$. The combined organic fractions were washed with saturated brine and dried over anh. Na—Mg sulfate. After evaporation, the residue was red issolved in 50 ml alcohol and allowed to crystallize at 4° C.

The dicarboxylic acid was titrated (0.52 g in 9 ml of $H_2O$) with an excess of NaOH 0.2N and back titration with HCl 0.2N. The results indicated that the substitution was 74%.

EXAMPLE 11

Two g (0.28 mEq) of the F108 dichloride from Example 7 were dissolved in 8 ml of dry DMF and there were added 0.54 g (2.9 mmol) of potassium phthalimide. The mixture was stirred overnight at 90° C. after which it was cooled and filtered over celite. The solution was heated to 50° C., 30 ml of ether were added and, upon cooling, a solid formed; yield 1.46 g after crystallization from EtOH (20 ml)/ether (50 ml). Better yields and purer product were experienced when the potassim phthalimide was added in form of a solution in formamide.

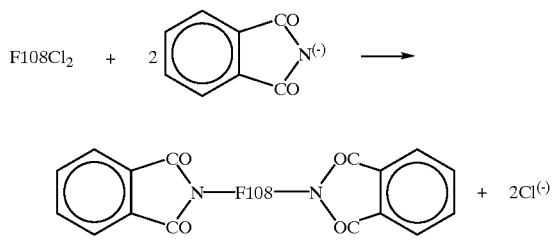

EXAMPLE 12

The compound of the previous Example (1.46 g, 0.2 mEq) was dissolved in 9 ml EtOH, and there were added 0.1 ml (2 mmol) of hydrazine hydrate. After one night at room temperature, the solution was diluted with 10 ml EtOH and refluxed for 3 hrs. Then the solvent was removed under reduced pressure, the residue was dissolved in 8 ml EtOH and a solid was precipitated by the addition of 40 ml ether. The solid was collected, washed with ether, dissolved in 8 ml ethanol, and 0.11 ml (2 mmol) of AcOH were added. The mixture was heated to 50° C., 50 ml of ether were added thereto and it was left to crystallize. White crystals (1.24 g) of diamino-F108 were collected and analyzed. titration of the —NH2 groups showed that the substitution was substantially 100%.

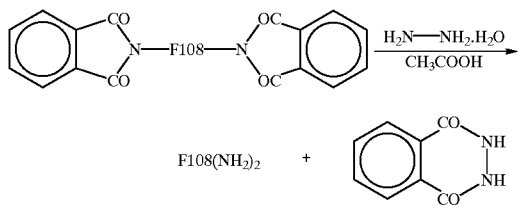

EXAMPLE 13

F108 (21 g, 3 mEq OH) were dried by azeotropic distillation in toluene and thereafter converted to a solution (120 ml) of the corresponding dipotassium alkoxyde as disclosed in Example 8. Sixty ml of this solution were reacted under agitation with 1.82 ml (15 mmol) of bromoacetaldehyde dimethyl acetal. The yellow solution was refluxed overnight whereby it became orange and turbid. It was filtered on celite, concentrated on the rotavapor and diluted with 120 ml ether, whereby it crystallized on standing. The solid was collected and dissolved in 50 ml ETOH, the ethanol solution was treated with charcoal, filtered and diluted with 40 ml ether. After cooling to 4° C., crystals of F108 diacetaldehyde dimethylacetal (9.05 g) had formed which were collected dried and analyzed.

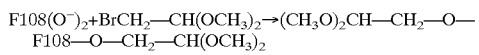

EXAMPLE 14

F108 (7.5 g, 1.07 mEq OH) was dissolved in 30 ml CCl$_4$ at 50° C. the solution was filtered and 0.27 ml (1.1 mEq) of tri-n.butylamine were added at room temperature followed by 1.07 g (3.6 mmol) of Bis(trichloromethyl)carbonate (triphosgene), this being equivalent to 10.8 mmol of COCl$_2$. After 1.5 hrs at room temperature, the solution was heated for 20 hrs at 50° C., then it was evaporated under vacuum to completely remove the HCl and phosgene excess.

The residue was dissolved in 30 ml CCl$_4$ and diluted with 80 ml of ether. The solid formed was collected at 4° C., washed with ether and redissolved in 30 ml CCl$_4$.

A solution was made containing 1.9 g (14.3 mmol) of t.butyl carbazate and 0.2 ml (0.8 mEq) of tributylamine in 2 ml of CCl$_4$. To this were added 20 ml of the above solution of F108 dichloroformate (0.715 mEq). After 18 hrs at 50° C., the solution was filtered and precipitated by the addition of 50 ml of ether and cooling to 4° C. The solid was crystallized in AcOEt/ether (20 ml/50 ml) to give 4.21 g.

The di(hydrazide-COO-t.Bu) compound in 8 ml CH$_2$Cl$_2$ was treated with 8 ml of TFA for deprotection as disclosed in Example 4. After 3 hrs at room temperature, the mixture was evaporated under vacuum, the residue redissolved in 15 ml CH$_2$Cl$_2$ and a solid precipitated by the addition of 90 ml of ether. This solid was crystallized from 20 ml EtOH+0.5 ml tributylamine, the solution being left overnight at 4° C. Yield 4.04 g of F108-dicarbazate (urethanehydrazide)

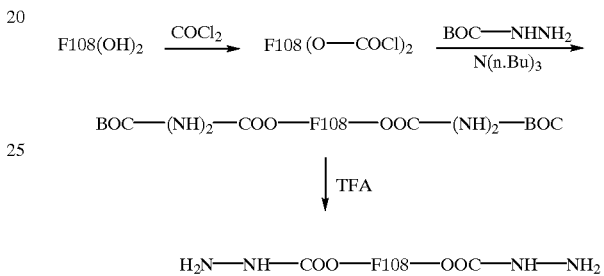

EXAMPLE 15

To a solution of 0.1 ml (0.4 mmol) of tributylamine and 0.5 ml (7.2 mmol) of ethylene diamine in 2 ml of CCl$_4$ were added 10 ml (0.36 mEq) of the F108-dichloroformate solution of Example 13. The solution was heated for 18 hrs at 50° C., it was diluted with 10 ml of methanol, filtered and a solid precipitated by 50 ml of ether. The solid was collected and recrystallized in AcOEt (10 ml)/ether (30 ml); yield 2.25 g of H$_2$N—(CH$_2$)$_2$—NH—COO—F108—OOC—NH—(CH$_2$)$_2$—NH$_2$. Titration of the —NH$_2$ groups by usual means showed that the substitution rate was about 60%.

EXAMPLE 16

In 100 ml of ether were dissolved 13.22 g (0.1 mol) of tert.butyl carbazate and 15.4 ml (0.11 mol) of triethylamine. Under cooling (0 to 5° C.) there were slowly added (in about 0.5 hr) 8.9 ml (0.1 mol) of bromoacetyl bromide. At the end, the temperature was allowed to come back to ambient and the precipitated triethyl ammonium bromide was removed by filtration (19.86 g=near theory). the red filtrate was chromatographed on silica (24 cm column; 200 ml) using ether as the eluent (100+250 ml). the yellow eluate was concentrated to about 80 ml and hexane was added until turbidity appeared. Crystals readily formed thereafter on shaking; the latter were collected at 4° C., yield 21.46 g, 85%.

The obtained product (tert-butyl N-bromoacetylcarbazate was reacted with the potassium salt of F108 like in Examples 8 and 13 and thereafter the t.Bu group was removed with TFA. There was thus obtained the hydrazide corresponding to the product obtained in Example 9.

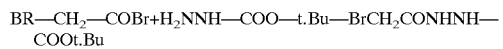

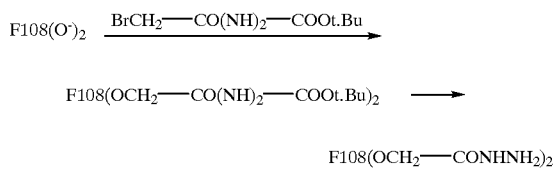

The linkers produced according to Examples 1–16 were successfuly used to associate drugs or signal generator moieties (I) and bioactive targeting molecules (II) to provide efficient vectors for the transport of (I) to sites in the organism having receptor affinity for (II).

If in the previous Examples the Pluronic® F108 amphiphilic compound was replaced by other copolymers having OH or $NH_2$ terminated hydrophilic polyalkyleneoxy segments, similar results were obtained, the resulting corresponding linker products being usable to bridge moieties (I) and (II) as said above. Among such copolymers, one may cite the Pluronics® and Synperonics® of various structures falling within the specifications of this invention, these structures involving various hydrophilic and hydrophobic sequences of different lengths. Other Poloxamers® and Poloxamines® as well as other convenient amphiphiles belonging to the brands known under the general registered names of Solulan®, Brij®, Mirj®, Tweer®, Triton®, Span®, etc., are also possible under special conditions.

EXAMPLE 17

(a) Preparation of (IfL) linker-magnetite particles.

In 40 ml of water, there were dissolved 81.1 mg (0.3 mmole) of $FeCl_3.6H_2O$ and 56.9 mg (0.3 mmole) of $FeCl_2.4H_2O$ (total Fe=0.6 mmole or 33.5 mg) To this were added 0.1 mCi of $^{59}Fe$ (tracer quantity) in the form $FeCl_3$.

The mixture was stirred and an aqueous 7.5% solution of ammonia was added dropwise until the pH reached a stable value of 8.6. A suspension of black particles formed which was heated for 5 min at 75° C. and the particles were allowed to settle at room temperature. The precipitate was washed three times by decantation with portions of 100 ml of water, after which it was again suspended in 60 ml of water under agitation. The iron concentration of this suspension was 0.5 mg/ml.

To 10 ml of this suspension (5 mg of Fe) were added (as component (a) 100 mg of the sodium salt of dipalmitoylphosphatidic acid (DPPA.Na) and sonication was effected for 20 min (BRANSON 250 Sonifer, ⅛" microprobe, output 20 (15–20 W). The temperature which rose to about 68° C. during sonication was allowed to drop to room temperature, and there were added (as component (b) 100 mg of Pluronic® $(NH_2)_2$ as prepared in Example 12 (or identically modified amphiphiles such as Synperonic® from ICI, or Poloxamer® 338). Sonication was then resumed for 15 min under the aforementioned conditions.

The obtained suspension of coated particles (Sample SBPA-$NH_2$) therefore contained, per ml, 0.5 mg of iron, 10 mg of DPPA and 10 mg of the derivatized Pluronic® $(NH_2)_2$ surfactant (weight ratio of (a) to (b)=1:1). Measurements by means of a particle counter apparatus (Nicomp 370 HDL-NPSS of Particle Sizing Systems, Santa Barbara, Calif., USA) indicated that, depending on the run, the average particle size was in the range 50–100 nm (±20–40%).

Other samples (see below) were prepared identically with the other derivatized amphiphles disclosed in the previous examples:

| Derivatized amphiphile | Example No | Sample code |
|---|---|---|
| F108 (underivatized) | (for controls) | SBPA-Ctrl |
| F108$(NHNH_2)_2$ | 6 | SBPA-Hz |
| F108$(OOC—NHNH_2)_2$ | 14 | SBPA-COHz |
| F108$(OCH_2—CONHNH_2)_2$ | 9 | SBPA-MeCOHz |

(b) Preparation of conjugates (IfL-II)

Ten ml of sample SBPA-$NH_2$ (see above under a) were centrifugated for 1 hr under 27'000 g. The undernatant residue was taken with 2.5 ml of 100 mM borate buffer (pH 8.2) [or phosphate-free isotonic solution] to provide a suspension containing 2 mg of iron/ml.

To 1 ml of the suspension were added 5 μmol of the couple biotin-NHS (NHS=N-hydroxy succinimide) available from Fluka A. G., Switzerland, neat, or as a concentrated DMSO solution. The mixture was agitated for 2 hrs at room temperature (room temperature), then it was dialyzed 4 succesive times against distilled water to give a purified sample of the desired magnetite-biotin conjugate labeled SBPA-NH-Bio.

Similar reactions were carried out between SBPA-$NH_2$ and other targeting factors (II), respectively, lactose isothiocyanate and folate-NHS (prepared according to J. Biol. Chem. 269 (1994) 3198–3204), to give respectively SBPA-NH-Lac and SBPA-NH-Fol. Coupling with the "RGD" peptide (H-GlyArg-Gly-Asp-Ser-Cys-OH) to give SBPA-NH-RGD was effected with the additional assistance of sSMBP [N-hydroxysulfosuccinimidyl-(4-maleinimidophenyl)-butyrate] according to the following scheme:

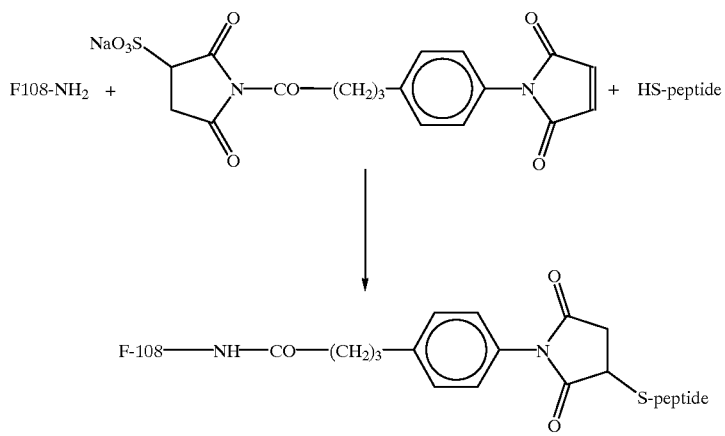

The procedure was as follows: a residue of centrifugation of a SBPA-NH$_2$ sample [obtained as under b), see above, in connection with the coupling with biotin] was suspended in 100 mM Hepes buffer, pH 7, to a concentration of 2 mg Fe/ml. To 1 ml of the iron suspension were added 5 μmol of sSMPB and the mixture was incubated for 2 hrs at room temperature. The product suspension was purified from excess reagent by gel-filtration chromatography (column G25). The purified Hepes suspension of SBPA-maleinimide was reacted overnight with a quantity of 2.5 μmol per mgFe of the thiol-derivatized peptide in the presence of EDTA (10 mM), then the excess reagents were eliminated by extensive dialysis against Hepes.

Controls were made also by "pseudocoupling" (under the foregoing conditions) magnetite particles carrying underivatized F108 with the above homing factors.

The foregoing targeted (and control) preparations were filtered on 0.2 μm membranes and tested both in vitro (avidin and THP1 receptors) and in vivo in laboratory rats.

For the in vitro testing, a control preparation was first prepared by activating the control sample SBPA-ctrl (see above) with biotin under the same conditions used for making preparation SBPA-NH-Bio. Then, both preparations were diluted to a series of concentrations corresponding to 60, 30, 15, 7.5 and 3.75 mg/ml of iron, respectively. The various dilutions were then tested by inoculating into microtiter plates previously incubated with avidin. After 4 hrs, the plates were washed from non-adsorbed materials and the bound iron ascertained by conventional analysis (thioglycollate). The results are presented in the form of the following graph in which the adsorbed iron ("Y" axis) is plotted against the iron in the foregoing dilutions ("X" axis). The curve denoting the behavior of SBPA-NH-Bio is marked with "♦"'s; the control curve is marked with "□"'s. The graph clearly demonstrates that the targeted magnetic particles have much greater affinity for avidin than the non-targeted ones.

Further in vitro tests in connection with the binding of $^{59}$Fe-labeled preparations of SBPA-RGD (control: SBPA-cys) were effected using cell lines for expression of the corresponding receptor. For this, U937 strain samples containing various concentrations of the preparations to be tested were cultivated for 48 hrs in standard media activated with 50 nM PMA (phorbol-12-myristate-13-acetate), then incubated for 1 hr at 37° C. The cells were washed in cold PBS, detached and radiocounted. From the measurements, the amount of iron-tagged cells relative to the controls could be ascertained.

The results are gathered in Table 1. They show that the amount of iron delivered by the SBPA-targeted particles is significantly greater than that from the controls.

TABLE 1

| | mean ng of Fe for $10^6$ cells (standard dev.) | | |
|---|---|---|---|
| | 10 | 30 | 100 |
| SBPA-rgd | 74 (13.2) | 181 (31) | 854 (4.5) |
| SBPA-cys | 42 (0.8) | 154 (14.9) | 427 (120) |

In a similar way, the binding of the $^{55}$Fe-SBPA-folate system (see above) was tested for affinity to the human KB cell line expressing folate receptors. KB cells were cultured as described in P.N.A.S. 92 (1995) 3318–3322 and incubated for 2 hrs at 37° C. with various concentrations of $^{55}$Fe-SBPA-folate. As the control, there was used a preparation containing $^{55}$Fe-SBPA, F108(OH) "pseudo-coupled" to folate.

The results are presented in the Table 2 below which show the iron concentration (mean values and standard deviation within brackets) retained in the media (in the presence and in the absence of additional foetal calf serum [FCS]).

TABLE 2

| | mg of Fe/ml in culture medium | | |
|---|---|---|---|
| Fe(ng)/$10^6$ cells | 10 | 30 | 100 |
| SBPA-folate | 111 (7.5) | 361 (28.5) | 1170 (53) |
| SBPA-folate + FCS | 77.5 (8.5) | 228 (27.5) | 557 (54.8) |
| Control | 124 (25.89) | 317 (37) | 739 (47) |
| Control + FCS | 99.7 (3.2) | 245 (10.2) | 611 (45) |

For in vivo tests, the preparations (diluted 20 fold) were injected in the caudal vein of the experimental rats (starting time $t_0$); then after various periods of time ($t_{10}$ min to $t_{120}$ min), blood samples were taken and analyzed for iron concentration. The results are gathered (expressed in % of the injected dose) in the Table 3 below. (A=SBPA-Ctrl; B=SBPA-NH-; "+" indicates there was no coupling between "A" and the targeting compound).

TABLE 3

| Time (min) | A | B − Lac | A + Lac | B − Bio | A + Bio | B − Fol | A + Fol | B − RGD |
|---|---|---|---|---|---|---|---|---|
| 10 | 87.9 | 87.8 | 85.3 | 94.1 | 96.1 | 9.1 | 91.3 | 91.7 |
| 30 | 85.8 | 66.5 | 72.6 | 68.9 | 76.2 | 0.4 | 74.3 | 71.9 |
| 60 | 80.4 | 33.9 | 31.3 | 34.6 | 43.9 | 0.7 | 26.7 | 22.4 |
| 90 | 76.7 | 25.4 | 10.3 | 24.6 | 22.9 | 0.6 | 9.9 | 8.1 |
| 120 | 66.5 | 19.6 | 4.3 | 18.0 | 13.9 | 0.5 | 5.6 | 4.6 |

The results of the foregoing Table indicate that, with the exeption of one case (B-Fol), the conjugates remained in the circulation for an appreciable length of time, actually longer than the uncoupled mixtures; this indicates that they are not rapidly removed by the liver and can be carried efficiently to the selected site. The B-Fol case is still unexplained, but its fate is probably due to some unidentified artefact.

EXAMPLE 18

The DTPA mono- and di-stearyl esters of formulae

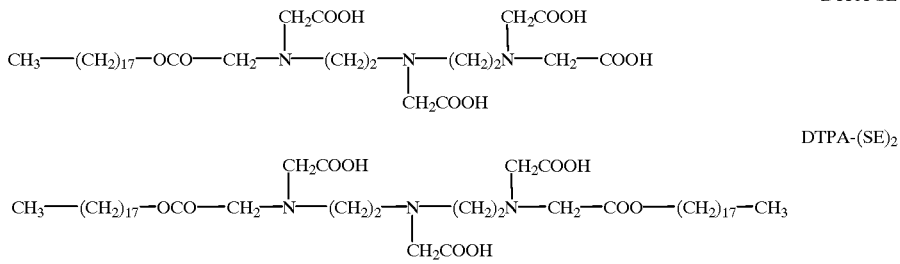

and the corresponding gadolinium chelates (Gd-DTPASE) and (Gd-DTPA(SE)$_2$), were prepared as disclosed in G. W. Kabalka et al., Magnetic Resonance in Medicine 8 (1988) 89–95. The DTPA anhydride required in the synthesis was made according to Eckelman et al., J. Pharm. Sci. 64 (1975) 704–706. The purity of the imaging agents was checked by measuring the gadolinium content by usual means (decomplexing in 2N hydrochloric acid and titrating with EDTA solution; indicator, Xylenol-orange). This analysis gave results substantially near theory.

A hundred mg of Gd-DTPA-SE (0.127 mmol) and 200 mg of dipalmitoylphosphatidic acid (DPPA·Na) were dissolved in 25 ml of a 1/1 mixture of MeOH and CHCl$_3$. The solution was evaporated to dryness under reduced pressure (Rotavapor, 72° C./15 Torr, 1.5 hrs), after which 20 ml of distilled water were added under agitation. The mixture was further homogenised by sonication for about 30 min at 70° C. (Branson Sonifier, output 40). To the above suspension were added 200 mg of modified Synperonic® F108(NH$_2$)$_2$as disclosed in Example 12 and sonication was resumed for a few minutes, whereby a stable optically clear suspension of submicronic particles (labelled "M1") in micellar form was obtained. The foregoing preparation was repeated, but this time using Gd-DTPA-(SE)$_2$ (0.095 mmol) instead of the Gd-DTPA-SE, to give a suspension labeled "M$_2$".

Proton spin relaxivities of the foregoing suspension were measured using a Minispec PC-120 (Bruker) apparatus, operating under 0.47 Tesla (20 MHz). EDM 510A (EDM= Experiment Definition Module) was used to measure the spin-lattice relaxation time $T_1$ by the "inversion recovery" method. EDM 610A was used to measure the spin-spin relaxation time $T_2$ by the CarrPurcell-Meiboom-Gill (GPMG) technique. The relaxivities ($r_1$ and $r_2$) expressed as r in $[mMs]^{-1} = 1/T$ for a 1 mM concentration are presented in Table 4.

When the foregoing preparation was coupled to selected homing factors (II) as described in Example 17, corresponding administrable systems Gd-DTPA-SEfF108-NH-(II), and Gd-DTPA-(SE)$_2$fF108NH-(I) were obtained. In vivo tests were performed with rats, as in Example 17, and gave comparable results regarding blood circulation.

TABLE 4

| Sample | $r_1$ | $r_2$ | Size (nm) |
|---|---|---|---|
| "M1" | 36.0 | 35.0 | 60 ± 30 |
| "M2" | 30 | 31 | 80 ± 40 |

EXAMPLE 19

Magnetite micro particles coated with Synperonic®F108 derivatized with terminal NH$_2$ groups were coupled to the "RGD" peptide as described in Example 17 (b) to provide test sample labeled SBPA-RGD. Control (SBPA-ME) was made similarly but using mercaptoethanol instead of the peptide in the terminal coupling reaction. Dilutions of test and control were prepared containing respectively 66 and 33 μg of iron/ml. These are labeled SBPA-RGD(66 μg Fe/ml) and SBPA-RGD(33 μg Fe/ml), respectively, SBPA-ME(66 μg Fe/ml) and SBPA-ME(33 μg Fe/ml).

The neutrophil respiratory burst activity triggered by the addition of the RGD targeted system was tested as follows:

Fully viable granulocyte cultures were prepared as disclosed by Y. Kasuya et al. in J. Biomedical Materials Research 28 (1994) 397–404.

Then the following reagents were introduced into suitable microplate wells: (a) 150 μl of solution (2 mg/ml in Hank's BSS) of nitro blue tetrazolium (NBT). (b) 100 μl of the test or control samples diluted to the aforementioned values. (c) 50 μl of the purified granulocyte preparation containing 5×10$^6$ cells/ml in HBSS. Then, incubation at 37° C. was carried out for various lengths of time.

The response of the living cells is checked by the progressive increase of absorbance at 540 nm due to the reduction of the dye (yellow to blue) by the O$_2$− generated during incubation. An additional plate containing the same mixture in 10 μM iodoacetamide is used as a color reference; its absorbance is subtracted from each time measurement of the tests or controls.

Figure 4:
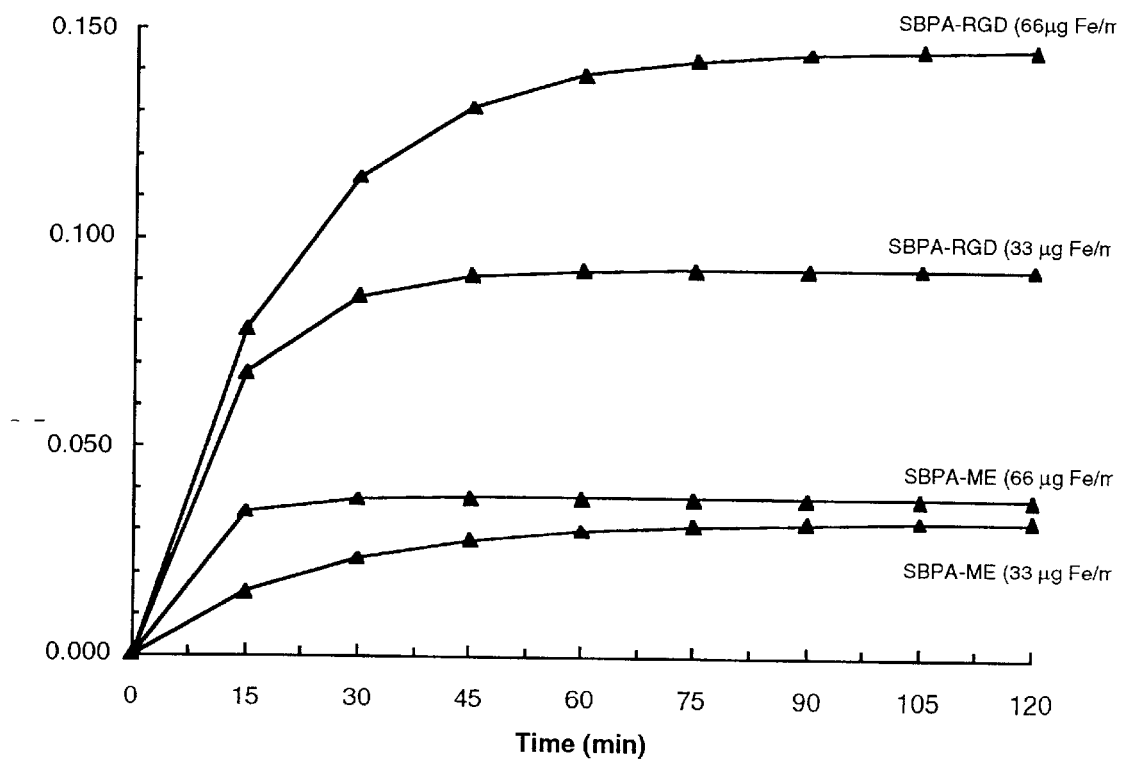
FIG. 4 is a graph showing the activity toward cultures of cellular neutrophils of a system comprising magnetic microparticles (SBPA) equiped with a chemotactic targeting factor (RGD peptide) via a linker (derivatized amphiphile) of the invention.

Results of the foregoing experiments are presented in the graph of FIG. 4 which show the considerable activity of the systems according to the invention.

EXAMPLE 20

Preparation of SBPA-maleinimidophenyl-butyramide

Ten ml of sample SBPA-NH$_2$ (see above under Example 17) were centrifuged for 1 hr under 27'000 g. The undernatant residue was taken with 100 mM HEPES buffer (pH 7.0) and diluted to 2 mg Fe/ml. To this were added 2.5 μmole of sulfosuccinimidyl-4[p-maleinimidophenyl]-butyrate (sulfo-SMPB) and the mixture was incubated for 2 hrs at room temperature Excess reagent was eliminated by adding EDTA (10 mM) and centrifugation (2 min, 100 g). The residue was resuspended in HEPES (2.5 mg Fe/ml).

EXAMPLE 21

Preparation of the S-acetylthioacetate of the hexapeptide f-Me-Leu-PheMe-Tyr-Lys.

6 μmol of the hexapeptide (prepared as from EP-A-0 398 143) were dissolved in DMSO to make a concentration of 10 mg/ml and 1 equiv. of N-hydroxysuccinimidyl-S-thioacetate (SATA) in the form of a 14 mg/ml DMSO solution was admixed; thereafter, N-ethylmorpholine was added to bring the apparent pH to 8 (moist pH strip). After 1 hr, the mixture was diluted 20 fold with H$_2$O and loaded on a HPLC chromatography cartridge equilibrated in water (C18 Bond Elut cartridge, eluent 80% aqeous acetonitrile). The thio-acetylated peptide appeared in the 18.77 min fraction which was dried to a solid; the latter was redissolved in a little DMSO.

EXAMPLE 22

Preparation of the hexapeptide coupled to the SBPA magnetite particles.

The hexapeptide S-acetylthioacetate (2 mg) in DMSO solution was added to a HEPES solution of the SBPA-maleininimide derivatized iron oxide particles (2.5 mg Fe) prepared as disclosed in Example 20. The HEPES buffer used also contained EDTA (2.5 mM) and hydroxylamine (50 mM); the hydroxylamine acts as a deacetylation reagent The mixture was kept at room temperature for 2 hrs, then the iron oxide particles were isolated by centrigugation, resuspended in buffer and extensively dialyzed for purification.

EXAMPLE 23

Testing of the magnetite-chemoattractant peptide conjugate—affinity with granulocytes.

Tissue injury and inflammation by bacterial infection induce granulocyte (PMN) and mononuclear phagocyte formation in response to the chemotactic peptides produced on the infection site. As acknowledged in Example 19, granulocytes will produce $O_2^-$ radicals which can be assayed by the reduction of the dye Nitro Blue Tetrazolium (NBT) absorbing at 540 nm.

Neutrophils were isolated from fresh buffy coats and cultured according to Magn.Res.Imaging 13 (1995) 393–400. The rate of NBT reduction was measured directly in the cells cultured in microplates. The assay media comprised 150 μl of NBT solution (2 mg/ml), 100 μl of the conjugate solution (this including various concentration samples) to which were added 50 μl of PMN (2.5·10$^5$ cells). Iodoacetamide (an inhibitor of oxidative burst) was added to the medium in the photometer reference well (to 10 mM final concentration), the cells having been preincubated for 10 min at 37° C. in 10 mM iodoacetamide. The complete details of the assay are disclosed in "Methods in Enzymology" 132, 417 Academic Press 1987.

Figure 5A:
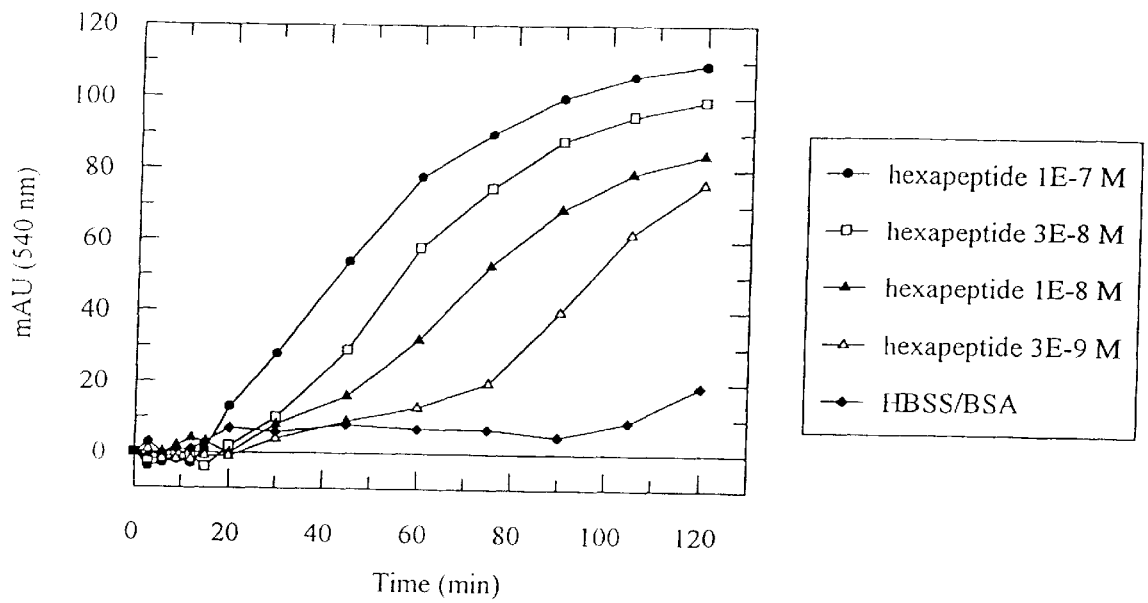
FIGS. 5 (a and b) are graphs showing the rate of reduction of NBT by human PMN stimulated by magnetite-labeled hexapeptide.
Figure 5B:
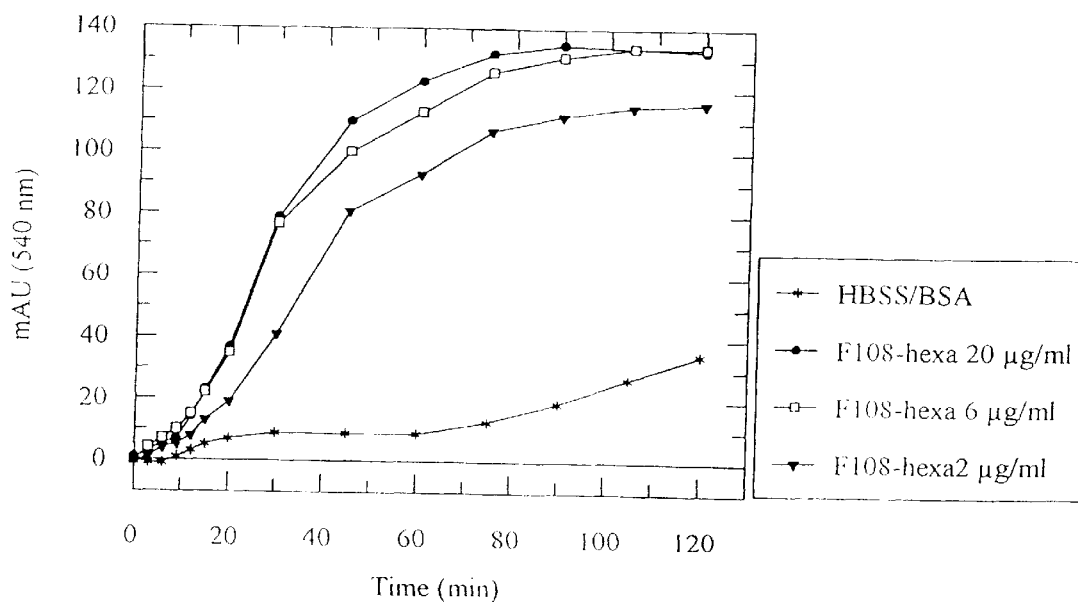

In the graph (a) of FIG. 5, there are respectively shown the rates of $O_2^-$ production by granulocytes in response to various dlutions (identified by the iron concentrations) of the SBPA-chemoattractant synthetic peptide. The capacity of PMN to be stimulated in a dose-dependent manner by the SBPA-hexapeptide is evidenced of the presence of the magnetite particles coupled to the chemoattractant. In the controls (b), the effect of the magnetic particles alone, uncoupled to the peptide, is virtually naught.

The foregoing results have been further confirmed by radioactivity measurements ($^{59}$Fe-labeled conjugates) and T$_2$ proton relaxation parameters (NMR). For these experiments, freshly purified human PMN was incubated for 1 hr at 37° C. with various SBPA-peptide conjugates, then washed in cold PBS. The T$_2$ measurements showed that the incorpora-tion/association of iron from the conjugate gave an effect 6 to 43 times greater than with uncoupled magnetite particles.

In laboratory rats, tracer measurements after intraveinous injection of $^{59}$Fe-SBPA-hexapeptide samples showed a preferential transfer of the iron through the circulation toward traumatized sites.

EXAMPLE 24

The conjugation of magnetite particles with non-specific F(ab)$_2$' fragments.

Ten ml of sample SBPA-NH$_2$ (see above under Example 17) were entrifuged for 1 hr under 27'000 g. The undernatant residue was taken with 100 mM HEPES buffer (pH 7.0) and diluted to 2 mg Fe/ml. To this were added 2.5 μmole of sulfosuccinimidyl-4[p-maleinimidophenyl]-butyrate (sulfo-SMPB) and the mixture was incubated for 2 hrs at room temperature Excess reagent was eliminated by adding EDTA (10 mM) and centrifugation (2 min, 100 g). The residue was resuspended in HEPES (2.5 mg Fe/ml).

A sample of antibody (Ab=non-specific IgG) was digested for 20 hrs at 37° C. with pepsin (in 0.2M NaOAc, pH 4.2) and the fragments purified by affinity chromatography and gel filtration.

In order to expose the free —SH groups, the F(ab)2' fragments were incubated for 1 hr at 37° C. with a solution of 1.5 mg/ml in 0.2M NaOAc, pH 5 of 2-mercaptoethylamine (MEA) to obtain a solution of approximately 10 mM final peptide concentration. Then the modified Fab fragments were isolated and purified by gel filtration in 0.15M NH$_4$OAc, pH 6.8.

An amount (1 mg) of the reduced Ab fragment was added to 2 ml of the foregoing SBPA-NH-sSMPB solution (diluted to 2 mg Fe/ml) in the presence of EDTA (10mM). The solution was left overnight at room temperature unde nitrogen; then it was chromatographed on sepharose 4B equilibrated in PBS, whereby unconjugated Fab was eliminated. Identification of the remaining desired compound was established by analysis using conventional means (iron and peptide determination).

EXAMPLE 25

To a solution of selected antibody (Ab) (2.5 mg/ml in PBS, pH 6) were added at 0° C. a quantity of 0.5M aqueous periodate solution in order to achieve a 22 mM NaIO$_4$ solution. the mixture was left to incubate in the dark on ice for 75 min, then 1,3-diamino-2-propanol (to make 30 mM) was added to stop the reaction. The pH was lowered to 4 with AcOH and the oxidized glycoprotein (generation of reactive —CO groups) was desalted by gel filtration on a Parmacia Superose 12 column.

Two ml of a solution of the foregoing oxidized Ab (1.5 g/ml in 0.1M NaOAc, pH 4.6–5.3) were added to 1 ml of a SBPA—OCO—NH—NH$_2$ solution containing 4 mg Fe/ml (code SBPA-COHz, see Examples 14 and 17) and the mixture was incubated for 20 hrs at room temperature whereby hydrazone bonds formed.

Before isolation of the labeled magnetic particles, reduction of the hydrazone function was effected using 0.2M sodium cyanoborohydride at pH 4.6. The Ab-SBPA conjugate was thereafter separated by gel filtration on a Sepharose 4B column.

EXAMPLE 26

In a variant from the procedure of Example 17, an adduct (L-II) involving a derivatized amphiphile linker (Synperonic® F108-NH$_2$) and a targeting peptide (folate-NHS) was first prepared and thereafter conjugated with signal generating magnetic iron particles to give exemplified system (IfL-II). As a starting ingredient, there was used a concentrated solution (100–180 mg/ml) of derivatized Synperonic® F108-NH$_2$ (see Example 12) in DMSO.

To an amount of this solution was added 1 molar equivalent of the modified folate-NHS peptide (see Example 17) and sufficient N-ethylmorpholine to bring the pH to 8.2 (moist strips). After 24 hrs standing at room temperature, unreacted ligand was removed by gel-filtration chromatography and the F108-peptide conjugate further purified by repeated dialysis against pure water. The yield of folate-coupled F108 was determined spectrophotometrically at 365 nm to be 0.63 mole of folate/mole of F108.

TABLE 6

| | mg of Fe/ml in culture medium | | |
|---|---|---|---|
| Fe (ng)/10$^6$ cells | 10 | 30 | 100 |
| SBPA-folate | 1060 (142) | 2010 (98) | 3960 (413) |
| SBPA-folate + FCS | 543 (38.4) | 1410 (39.4) | 3620 (360) |
| Control | 132 (2.3) | 381 (30.7) | 1530 (201) |
| Control + FCS | 118 (12.7) | 434 (8.4) | 1500 (141) |

The adduct preparation was used as such to prepare the corresponding SBPA-folate system by sonication according to the technique disclosed in Example 17, section a), for making the SBPA-NH$_2$ adduct (IfL). The preparation was centrifugated and the pellet ressuspended in isotonic buffer. The binding capacity of the conjugate system to KB cells was effected exactly as described in Example 17 for the corresponding $^{59}$Fe-SBPA-folate conjugate adduct. The results compared to a same control are gathered in the Table 6 above.

Various surface active agents are identified above with reference to the names and/or product numbers provided by various suppliers. Poloxamers, also known as polyethylene-polypropylene glycol copolymers, are available as Pluronic® from the BASF Corp. The non-ionic surfactants Synperonic® are from ICI Chemicals and Polymers, Wilton, U.K. Polyoxyethylene stearates, a series of polyethoxylated derivatives of stearic acid, are available as Myrj® while the polyoxyethylene alkyl ethers are available as Brij. The Tween® products are known generally as polysorbates.

---

We claim:

1. Administrable molecular conjugate systems represented by the formula I⇌L-II wherein:

I is a magnetically responsive, MRI contrast ligand moiety carrying hydrophobic groups, II is a targeting factor moiety having bioaffinity for specific sites, organs or tissues in the body, and L is an amphiphilic bridging linker reactively functionalized and covalently linked to moiety II, said bridging linker L having hydrophobic and hydrophilic sequences in its molecule to non-covalently link to moiety I by affinity forces as represented by⇌ between the hydrophobic groups of I and the hydrophobic sequences of L.

2. The molecular conjugate systems of claim 1 wherein linker L has the formula (i)

$$Y(W\text{-}Z\text{-}R)_m \qquad (i)$$

wherein YW is an amphiphilic segment comprised of a hydrophobic-lipophilic sequence Y for non-covalently binding with moiety I and a hydrophilic-lipophobic sequence W connected covalently together, Z is a chemical bond, or an aliphatic intermediate segment, m is 1, 2, or 4 and R is a binder for effecting coupling with said targeting factor moiety II.

3. The systems of claim 2, in which the linker L has the formula (ii):

$$(RZWY)_2N\text{-}A\text{-}N(YWZR)_2 \qquad (ii)$$

in which A is a hydrophobic sequence, with the proviso that in formula (ii) one to three of the R's is hydrogen and that the linker L effects coupling with up to four targeting units.

4. The systems of claim 2, wherein when m is 4, Y has the formula A(Y')$_4$ in which A and Y' are hydrophobic aliphatic or arylaliphatic sequences optionally interrupted by heteroatoms.

5. The systems of claim 3, in which A is a group of formula=N(CH$_2$)$_p$N=, in which p is an integer from 2 to 6.

6. The systems of claim 2, wherein Y is polyalkyleneoxy chains in which alkylene designates linear or branched C$_3$-C$_8$ aliphatic units.

7. The systems of claim 6, wherein hydrophobic sequence Y is polyoxypropylene having 10–60 propylenoxy units.

8. The systems of claim 2, wherein hydrophilic sequence W is selected from polyoxymethylene and polyoxyethylene.

9. The systems of claim 8, wherein W is selected from polyoxyethylene having 50–150 polyethylenoxy units.

10. The systems of claim 2, wherein the relative lipophilicity and hydrophobicity of Y approximately matches with the relative hydrophilicity and lipophobicity of W so that the hydrophilic/lipophilic value is in the range of 10–35.

11. The systems of claims 1, in which the ligand (I) is selected from paramagnetic species and magnetic submicronic particles, and the factor (II) is selected from tissue and surface-specific homing proteins, glycopeptides and carbohydrates.

12. The systems of claim 2, wherein m=2 and in which Y is polyoxypropylene of 48 propyleneoxy units and W is polyethyleneoxy of 127 ethyleneoxy units, WY a poloxamer.

13. The systems of claim 1, in which I is magnetic particles coated with a phosphatidic acid or a paramagnetic metal chelate of a polyamino polycarboxylic acid partially esterified with a hydrophobic long chain aliphatic acid, II is selected from the group consisting of tissue and cytospecific or surface specific homing proteins, glycopeptides and carbohydrates, and L is a derivatized nonionic surfactant.

14. A method for making the systems of claim 1, which comprises selecting amphiphilic linkers L comprising hydrophilic and hydrophobic sequences, then (a) providing by derivatization said linkers L with chemically reactive groups, (b) covalently binding via said reactive groups with a targeting factor II and (c) non-covalently binding via said hydrophobic sequences with a magnetically responsive compound, thus obtaining the systems of formula I⇌L-II.

15. The method of claim 14, whereby an intermediate of structure (L-II) is obtained after step (b), step (c) being effected using said intermediate (L-II).

16. The method of claim 14, wherein step (c) is effected before step (b), whereby an intermediate (IfL) is obtained from step (c).

17. The method of claim 14, wherein the derivatized linker functions are selected from —NH$_2$ or NHR[1] where R' is a lower alkyl, —CHO free or in the form of dialkyl acetal, —CO—NH—NH$_2$, —O—CO—NH—NH$_2$, —COOH, —SH, —COCl, or —O—COCl.

18. The method of claim 14, in which the derivatized linker L is a nonionic surfactant; ligand moiety I is selected from the group consisting of magnetite submicronic particles coated with a phosphatidic acid, and hydrophobized paramagnetic chelates; and II is selected from the group consisting of biotin, lactose, folate, and peptide.

19. An intermediate I⇌L for covalently binding to tissue or surface proteins, glycoproteins or carbohydrates, wherein I is a magnetically responsive, MRI contrast, ligand moiety carrying hydrophobic groups and L is an amphiphilic bridging linker reactively functionalized to link to said tissue or surface protein and having hydrophobic and hydrophilic sequences in its molecule to non-covalently link to I by affinity forces as represented by ⇆ between the hydrophobic groups of I and the hydrophobic sequences of L.

20. An intermediate L-II for non-covalently linking to a magnetically responsive, MRI contrast ligand moiety carrying hydrophobic groups, wherein II is a targeting moiety having bioaffinity for specific sites, organs or tissues in the body and L is an amphiphilic bridging linker reactively functionalized and covalently linked to moiety II, said bridging linker L having hydrophobic and hydrophilic sequences in its molecule to non-covalently link to the MRI contrast ligand by non-covalent affinity forces between the hydrophobic groups of the MRI contrast ligand and the hydrophobic sequences of L.

21. A method of MRI imaging a human or animal patient comprising the steps of (a) administering a molecular conjugate system of claim 1 to said patient and thereafter (b) MRI imaging said patient.

22. A method of MRI imaging a human or animal patient comprising the steps of (a) administering a molecular conjugate system of claim 2 to said patient and thereafter (b) MRI imaging said patient.

23. The systems of claim 2 wherein YW is an amphiphilic surfactant selected from the group consisting of poloxamers, non-ionic surfactants, polyoxyethylene stearates, polyoxyethylene alkyl ethers and polysorbates.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 6 amino acids
      (B) TYPE: amino acid
      (C) STRANDEDNESS:
      (D) TOPOLOGY: linear (ii) MOLECULE TYPE: peptide (xi) SEQUENCE DESCRIPTION: SEQ ID NO:1:

Gly Arg Gly Asp Ser Cys
   1                5

(2) INFORMATION FOR SEQ ID NO:2:

(i) SEQUENCE CHARACTERISTICS:
      (A) LENGTH: 6 amino acids
      (B) TYPE: amino acid
      (C) STRANDEDNESS:
      (D) TOPOLOGY: linear (ii) MOLECULE TYPE: peptide (ix) FEATURE:

```
      (A) NAME/KEY: Modified-site
      (B) LOCATION: 1
      (D) OTHER INFORMATION: /product= "Nle"

(ix) FEATURE:
      (A) NAME/KEY: Modified-site
      (B) LOCATION: 4
      (D) OTHER INFORMATION: /product= "Nle"

(xi) SEQUENCE DESCRIPTION: SEQ ID NO:2:

Xaa Leu Phe Xaa Tyr Lys
1               5
```